(12) United States Patent
Canale

(10) Patent No.: US 12,105,074 B2
(45) Date of Patent: Oct. 1, 2024

(54) METHODS OF PREPARING AND ANALYZING BREAST MILK

(71) Applicant: Stephanie Canale, Santa Monica, CA (US)

(72) Inventor: Stephanie Canale, Santa Monica, CA (US)

( * ) Notice: Subject to any disclaimer, the term of this patent is extended or adjusted under 35 U.S.C. 154(b) by 9 days.

(21) Appl. No.: 17/488,604

(22) Filed: Sep. 29, 2021

(65) Prior Publication Data

US 2022/0099647 A1    Mar. 31, 2022

Related U.S. Application Data

(60) Provisional application No. 63/085,537, filed on Sep. 30, 2020.

(51) Int. Cl.
| | |
|---|---|
| *G01N 33/14* | (2006.01) |
| *G01N 1/40* | (2006.01) |
| *G01N 1/42* | (2006.01) |
| *G01N 30/02* | (2006.01) |
| *G01N 30/72* | (2006.01) |

(52) U.S. Cl.
CPC ........... *G01N 33/14* (2013.01); *G01N 1/4055* (2013.01); *G01N 1/4077* (2013.01); *G01N 1/42* (2013.01); *G01N 30/7206* (2013.01); *G01N 2001/4061* (2013.01); *G01N 2001/4088* (2013.01); *G01N 2030/025* (2013.01)

(58) Field of Classification Search
CPC .... G01N 33/14; G01N 1/4055; G01N 1/4077; G01N 1/42; G01N 30/7206; G01N 2001/4061; G01N 2001/4088; G01N 2030/025; G01N 30/88; G01N 2030/067; G01N 30/06; G01N 2030/8813; G01N 1/28

See application file for complete search history.

(56) References Cited

PUBLICATIONS

Chuang, Chih-Kuang, et al. "Comparison of free fatty acid content of human milk from Taiwanese mothers and infant formula." Taiwanese Journal of Obstetrics and Gynecology 52.4 (2013): 527-533. (Year: 2013).*

George, Alexandra D., et al. "Human milk lipidomics: Current techniques and methodologies." Nutrients 10.9 (2018): 1169. (Year: 2018).*

Morrison, William R., and Lloyd M. Smith. "Preparation of fatty acid methyl esters and dimethylacetals from lipids with boron fluoride-methanol." Journal of lipid research 5.4 (1964): 600-608. (Year: 1964).*

Supelco, "Product Information: 15716 Boron trifluoride—methanol solution." Merck KGaA (2018). 1-2. < https://www.sigmaaldrich.com/deepweb/assets/sigmaaldrich/product/documents/390/407/15716dat.pdf>. (Year: 2018).*

Chisaguano, Aida Maribel, et al. "Elaidic acid, vaccenic acid and rumenic acid (c 9, t 11-CLA) determination in human plasma phospholipids and human milk by fast gas chromatography." Analytical Methods 5.5 (2013): 1264-1272. (Year: 2013).*

Chen, Z. Y., et al. "Breast milk fatty acid composition: a comparative study between Hong Kong and Chongqing Chinese." Lipids 32.10 (1997): 1061-1067. (Year: 1997).*

Jiang, Jiajing, et al. "Changes in fatty acid composition of human milk over lactation stages and relationship with dietary intake in Chinese women." Food & function 7.7 (2016): 3154-3162. (Year: 2016).*

Ruiz-Rodriguez, Alejandro, Guillermo Reglero, and Elena Ibañez. "Recent trends in the advanced analysis of bioactive fatty acids." Journal of pharmaceutical and biomedical analysis 51.2 (2010): 305-326. (Year: 2010).*

Wu, Ke, et al. "Lactational changes of fatty acids and fat-soluble antioxidants in human milk from healthy Chinese mothers." British Journal of Nutrition 123.8 (2020): 841-848. (Year: 2020).*

Kamao, Maya, et al. "Quantification of fat-soluble vitamins in human breast milk by liquid chromatography-tandem mass spectrometry." Journal of Chromatography B 859.2 (2007): 192-200. (Year: 2007).*

Buchanan, Michael D., Katherine K. Stenerson, and Leonard M. Sidisky. SLB-IL111 for Fatty Acid Methyl Ester (FAME) Applications. Technical Report SIGMA-ALDRICH, 2011. Accessed Online: <https://www.labplus.co.kr/upload/tech/2015/12/1/cMcYAMYMYU_20151201174952706.pdf>. (Year: 2011).*

* cited by examiner

*Primary Examiner* — Jill A Warden
*Assistant Examiner* — Michael Paul Shimek
(74) *Attorney, Agent, or Firm* — Cusick IP, PLLC; Clinton J. Cusick, Esq.

(57) ABSTRACT

The present disclosure provides methods of preparing breast milk for analysis analyzing breast milk, determining reference ranges for analytes in breast milk and testing breast milk for a panel of analytes. Aspects of the present disclosure provide dietary and lifestyle recommendations for the lactating mother-based on measured concentration of analytes. Retesting is disclosed to measure the influence of maternal diet on breast milk composition.

4 Claims, No Drawings

METHODS OF PREPARING AND ANALYZING BREAST MILK

CROSS-REFERENCE TO RELATED APPLICATION

This application claims the benefit of U.S. Provisional Patent Application No. 63/085,537 filed Sep. 30, 2020, which is incorporated herein by reference in its entirety.

BACKGROUND OF THE INVENTION

Field of the Invention

The present general inventive concept is directed to a method of collecting and analyzing breast milk to determine the composition of a breast milk. Methods are directed to determining the presence of beneficial as well as harmful elements and compounds, comparing concentrations to desired levels, and providing dietary recommendations to modify the concentrations of analytes in successive breast milk samples.

Description of the Related Art

Breastfeeding rates have increased in the United States and Worldwide. The American Academy of Pediatrics (AAP), World Health Organization (WHO) and Center for Disease Control (CDC) recommend exclusive breastfeeding for the first 6 months of life and ideally until the age of one. It is the standard of care for premature infants in the NICU to receive human milk and it has been shown to be lifesaving. More women are choosing to use donor milk and the nutritional quality of human breast milk is unknown and of concern to mothers and health care providers. As human breast milk is recommended to be the sole source of nutrition for the first 6 months of life, and ideally until the age of 1, determining the nutritional composition of human milk is becoming increasingly important to evaluate the overall health and nutrition of infants. There currently exists a need in the industry for a process that analyzes human breast milk for essential vitamins and minerals and for testing milk for exposure to toxins and drugs.

Breastfed babies are less likely to develop allergies and GI, respiratory, or ear infections. They are also less likely to become overweight or develop diabetes later in life and have been shown to have a higher IQ. Breastfeeding mothers are less likely to develop diabetes and to experience breast or ovarian cancer. Studies in the past have avoided determining milk nutritional information at the level of an individual breastfeeding mother. Many studies have shown that maternal diet does not impact the concentration of micronutrients, minerals and Vitamins in human milk, and to date there is a belief by many that maternal milk analysis is not warranted. Older studies looked at pooled breast milk samples and did not account for the variations in diet. Some also included very small sample sizes (e.g., Hall et al. from 1979 studied 3 women). Other studies have looked at single samples and not recorded the daily variation within the same individual. In addition, variability in the detected breast milk composition was often due to differing laboratory methods used for the analyses. In addition, variability in the breast milk composition was often due to differing laboratory methods used for the analyses, including both direct energy quantification by combusting in a bomb calorimetry, and calculated energy estimates using Atwater energy multiplication factors for macronutrients such as protein, fat and carbohydrates. The methods used to measure protein also varied from both direct quantification of the true protein content, and quantification of the nitrogen only, which does not account for the presence of nitrogen in non-protein compounds. This has made it difficult to extract reliable data from many early studies.

Overall, prior efforts at analyzing breast milk composition were not directed at individual mothers, or individual samples and focused on the dietary impact. Small sample sizes were utilized or samples were pooled between individuals. The assumption that breast milk is consistent between nursing mothers or consistent over time belies a belief that breast milk composition does not vary during a feed, throughout the day or between mammary glands. Studies have not tracked a single nursing human's breast milk composition or nutritional content over time.

Further, there are large groups of breastfeeding supporters that suggest that human milk not be tested as it is simply unnecessary and may cause undue stress upon the lactating mother. There have been many news articles and statements made by La Leche League, baby friendly UNICEF, and the World Health Organization that state that human milk testing is not necessary. Despite widespread opposition to breastmilk testing, the medical community needs tools to help mothers breastfeed and develop the confidence to breastfeed for as long as possible. Many mothers stop breastfeeding before they want to because of difficulties and uncertainties they encounter. One of the largest difficulties nursing mothers encounter is uncertainty about the nutritional content of their breast milk. Being presented with known nutritional content of a baby formula creates uncertainty as to the better feeding alternative when nursing mothers do not have information about the breast milk they produce. Many mothers switch to formula or augment feeding with formula because they are unsure of the nutritional content of their breastmilk. Additional information can eliminate this uncertainty and provide confidence as to the benefits of breastfeeding. Additionally, there are links between a mother's diet and the content of her breastmilk. Testing of individual breast milk is required to provide individualized dietary guidance. Nursing women who learn about how diet affects their milk have been shown to breastfeed longer. Fifty percent of women stop breastfeeding because they simply believe their milk is "not good enough." Knowing nutrient concentrations can help build confidence in continued breastfeeding, but testing is difficult, and not common, or accessible.

Enzyme linked immunosorbent assay (ELISA) is a method for detecting and quantifying a specific protein in a complex mixture. Traditional laboratory approaches to human milk samples do not produce desirable results. Sample pre-treatment and detection methods are unreliable. This is likely due to the unique properties of human milk (e.g., containing large amounts of fats and carbohydrates). Traditional laboratory methods have been developed to analyze blood, plasma, urine or stool, for example. These substances do not contain significant amounts of fat or complex sugars. The complex stereochemistry of the oligosaccharides in human milk as well as their branched-chain structures results in structural diversity of oligosaccharides which are not found in other bodily fluids and confounds traditional laboratory methods. These macronutrients constitute >10% of human milk by weight, which affects the physical and chemical behavior of the sample and requires adjustments in the sample preparation protocol.

Prior methods of analyzing breast milk take a long time because it was not thought to be useful and some thought this would discourage breastfeeding. Prior art methods are not suitable for home use because it was thought to be unnecessary to test human milk and thought that human milk was not affected by maternal diet and consistent amongst all women. As a result, most breast milk analysis takes place in a hospital or laboratory setting and is not suitable for regular use by nursing mothers who are not experiencing health issues or seeking medical treatment.

Prior reliable or accurate results with low detection limits are not available for either B12, iron, or folate amongst other analytes. Using NMR to analyze docosahexaenoic acid in human milk (DHA) in human milk does not provide a reliable peak for quantitative analysis. This was likely due to the large amounts and variability of fatty acids and confounding effects of large quantities of fat and carbohydrates. Human milk cannot be tested at a regular laboratory as there are unknown norms for acceptable ranges of concentrations of analytes.

Prior attempts to analyze food samples with high lipid content such as milk have included a laborious saponification step prior to extraction of the fatty layer to eliminate interactions among lipids, lipid-soluble vitamins, and the matrix typically consisting of aqueous and fatty components. Overnight saponification was initially needed to analyze fat soluble vitamins such as vitamin A, D, E, and K. Overnight saponification is a very lengthy and expensive process to perform. What is needed is a more rapid sample preparation method.

Further, there are no standardized normative values for reference ranges for substances found in human milk. A breast milk sample cannot be ordered by a physician to be sent to a CLIA certified laboratory or other commercially available laboratory for analysis and is an "unknown bodily fluid" because there are no standardized published reference ranges.

What is needed is a set of nutrient guidance concentrations to determine if individual breast milk is nutritionally sufficient.

What is needed is a method of collecting and preparing breast milk samples for analysis that can be practiced by a user in a home or non-laboratory setting. What is needed is a useful set of dietary recommendations for nursing mothers based on the results of the analysis of their breast milk and comparison with nutrient guidance concentrations for providing dietary guidance. There is a need for mothers and their healthcare providers to analyze breast milk efficiently and accurately for nutritional contents, toxic metals, and drugs that may be present in human breast milk.

What is needed is a method of providing nutritional feedback based on measured nutrient concentrations in breast milk.

Maternal diet has a profound influence on the composition of human milk for some nutrients and breast milk can vary significantly from mother to mother. [move]

SUMMARY OF THE INVENTION

It is an aspect of the present invention to provide a method of collecting breast milk sample and preparing the sample for analysis that can be completed by a nursing mother in a home or non-laboratory setting. In an embodiment of the invention, the method comprises the steps of collecting milk from the same lactating individual over a 24-hour period and pooling that sample; storing the milk sample in a sterile test tube; freezing the milk sample; transporting the frozen milk sample to a laboratory; maintaining the frozen milk sample −80 to −20 degrees C.; thawing the frozen milk sample to room temperature; preparing the sample for analysis; determining a plurality of nutrient analyte concentrations; comparing measured concentrations of nutrient analytes in the sample against guidance concentrations of nutrient analytes; Providing dietary guidance and personalized dietary recommendations; and retesting to determine progress.

It is a further aspect of the invention to compare results of analysis of a breast milk sample with nutritional guidelines and dietary impacts to recommend a course of action to nursing mothers. Method comprising the steps of analyzing the milk for specific analytes, determining the reference ranges for each analyte and toxin, and providing dietary recommendations based on these results to the lactating mother.

Aspects of the present disclosure include methods of screening breast milk for a panel of toxins, comprising but not limited to mercury, cadmium, lead, arsenic, aluminum, silicon, platinum copper, nickel, beryllium, boron and chromium. Determined concentration of contaminant analytes can be compared with guidance concentrations of contaminant analytes. Health recommendation can be provided based on the measured concentration versus the guidance concentration for each contaminant analyte.

Quantifying a unit measurement of one or more analytes in the sample can comprise utilizing mass spectrometry (MS), Optical Emission Spectrometry (OES), liquid chromatography LC, and/or gas chromatography (GC). In some embodiments, MS is Inductively Coupled Plasma-MS (ICP-MS). In some embodiments, the OES is ICP-OES and any combination of the above to achieve the desired results of an analyte. Quantifying comprises quantifying the signal intensities detected for each analyte and comparing the signal intensities to a calibration curve for that analyte to determine the concentration of each analyte.

DETAILED DESCRIPTION OF INVENTION

Reference will now be made in detail to the presently preferred embodiments of the invention. Analysis of human milk can be conducted with liquid chromatography with tandem mass spectrometry: LC/MS/MS, gas chromatography coupled with mass spectrometry (GC/MS), and/or analysis using inductively coupled plasma mass spectrometry (ICP-MS), or inductively coupled plasma with optical emission spectrometry (ICP-OES) analysis.

In some embodiments, the method of the invention includes collecting a milk sample (e.g., one or more samples) comprising breast milk from the human that produced the breast milk. In certain embodiments, collecting the sample includes extracting, from the human, an amount of breast milk into a test tube. Extracting breast milk from the human can be performed using known techniques, such as, but not limited to, commercially available breast milk pumps, pumping breast milk by hand, and the like. The sample collection container can comprise a sterile test tube. Specifically, 5-30 ml of human milk can be collected in a sterile test tube. A nursing individual can pool together all expressed samples throughout a 24-hour period.

The method can comprise refrigerating and then freezing the test tube containing the breast milk until the breast milk is ready to be analyzed. The step is necessary to preserve the chemical and physical properties of the macronutrients that need to be analyzed in the human milk (HM). The method can comprise sending the frozen breast milk with frozen gel packs to a laboratory for analyzing the breast milk. Dry ice is not needed for shipment. If the sample is not frozen adequately, endogenous lipases have the opportunity to cause lipid hydrolysis resulting in inaccurate and misrepresentative HM lipid content for measurement. Storage at −20 degrees C. or −80 degrees C. stops enzyme activity within the samples and HM lipid integrity is best preserved.

Upon receipt by a laboratory, a sample can be stored in a freezer from −20 to −80 degrees Celsius until ready for processing. Sample preparation differs depending on the analytical instrument that is used.

The method further provides for removing the sample from the freezer, thawing the sample at room temperature, for example at least 20 degrees C., and homogenizing to produce a prepared milk sample. The prepared milk sample is then ready for analysis.

Example 1

LC/MS analysis to measure micronutrients including Vitamin A, D, E, K1, K2, folate and choline, the sample requires a stepwise purification process. a) Combining approximately 0.5 mL amount of prepared milk sample with approximately 10 mL of hexane and 1 mL of 5.4 M sodium methoxide in methanol solution to form a mixture. b) Vortexing the sample to form a hexane layer in the test tube. c) Separating the hexane layer. d) Filtration of the hexane layer with a silica cartridge. The sample extract is ready for analysis.

Example 2

GC/MS Analysis is used to measure fatty acids. The initial step in the analysis of lipids present in HM is separation of lipids from the rest of HM components. Steps of the method comprise: a) Liquid-liquid extraction (LLE) is used to separate analytes by their relative solubility in different immiscible liquids. The first step consists in taking 1 mL of HM sample and to wash it with chloroform, methanol and water in ratio of 1:2:0.8 respectively in a separating funnel. The funnel is closed and shaken gently by inverting the funnel multiple times. The funnel is inverted and the stopcock carefully opened to release excess vapor pressure if present. The separating funnel is set aside to allow for the complete separation of the phases. The mixture (HM+chloroform, methanol and water) separates into the bottom the organic phase with chloroform and breast milk lipids, and into the top aqueous phase with methanol, water, and containing carbohydrates and salts. The top and the bottom stopcock are then opened and the lower phase is released by gravitation collecting the separated breast milk lipids dissolved in chloroform. Following the lipid extraction from the HM sample, the analyte undergoes a chemical transesterification. Hydrolysis of the triacylglycerides (TAGs) following the derivatization of the released fatty acids (FA) to methylesters (FAMEs) for GC analysis. The derivatization is necessary otherwise the GC column will give a false reading that will show a band broadening with a false retention time. b) Dissolve the analyte in a nonpolar solvent such as hexane in a vessel. c) Add 2 mL BCl3-methanol, 12% w/w. d) Heat at 60° C. for 10 minutes. e) Cool the sample, then add 1 mL water and 1 mL hexane and shake the vessel. f) After the layers settle, collect the upper organic layer to a clean vial to provide a sample extract. The sample extract is ready for injection into GC apparatus.

Calibration of GC can be conducted before analysis of the sample. Inject 1.0 μL FAMEs standard solution into GC apparatus. Observe chromatogram for any interferences and make sure that all FAMEs in the standard solution have eluted and that the 19 FAME peaks are resolved, especially the Cl 8:1 trans and cis peaks. Determine the relative retention times for each of the FAMEs in the mixed standard solution relative to C 13:0 (internal standard). Define the concentration range within which the linear range of the method will be evaluated and established. The sample extract is then injected comprising 1.0 μL sample extract onto GC column.

Further, GC/MS is conductive for analysis of fatty acids in human milk. The sample extract can be analyzed with GC/MS as follows. GC/MS conditions.—Oven: initial temperature, 140 EC (hold 5 min), rate, 4.0 EC/min; final temperature, 240 EC; final time, 15.0 min. Zone temperatures: injector, 220 EC; split ratio, 40:1; carrier gas, helium; 0.6 mL/min; interface temperature, 280 EC. The equipment is preferably calibrated by autotuning prior to each series of analyses.

The relative retention times for each of the analytes are recorded from the GC chromatogram. Relative retention times are used to identify the FAMEs in the sample. Amounts of fatty acids are calculated from peak areas according to standards.

Example 3

Inductively coupled plasma mass spectrometry (ICP-MS) is a type of mass spectrometry that uses an inductively coupled plasma to ionize the sample. This is the preferred analytical technique for detecting metals and some non-metals in liquid samples present in low concentrations. This is the method of analysis used for calcium, iron, cyanocobalamin, heavy metals, and environmental toxins for example. In an embodiment of the invention, a method comprises the steps of:

a) Providing 1 ml of prepared milk sample. b) Homogenizing the prepared milk sample, after heating the sample to 40 degrees C. with inversion and vortexing. c) Digesting the homogenized sample by mixing with about 60-70% HNO3 and about 30% H2O2 in a 1:1 ratio. d) Holding mixture at a temperature of about 195° C. for a period of 20 to 45 minutes. f) cooling the mixture to room temperature and diluting the mixture to make a final volume of 50 ml with deionized water for analysis. g) Establishing a calibration curve using a standard solution with dwell time set at 50 milliseconds and thirty sweeps and three replicated with background correction are completed. h) Quantifying the signal intensities detected for each analyte and comparing the signal intensities to a calibration curve for that analyte to determine the concentration of each analyte.

Example 4

An alternate embodiment of the invention comprises preparation of a sample for ICP-MS or ICP-OES to determine concentrations of analytes including Vitamin A, Vitamin D and Vitamin E comprising the steps of: a) Adding 20 ml of prepared milk sample to a test tube b) Homogenizing the prepared milk sample, with inversion, vortexing and/or sonicating. c) Mixing 20 ml of the sample with: about 50 to 70 ml of 95% ethanol, about 10-30 ml of 50% (weight/volume) Kolliphor EL (KOL), about 40 to 60 mg of hydroquinone, and about 0.5 to 1.5 ml of 12% (weight/volume) sodium sulfide in water d) Saponifying the sample by heating the sample e) Extracting one or more analytes in the sample by: mixing the sample with a 1:1 ratio of petroleum ether and diethyl ether f) Washing the sample [with ethanol] and evaporating the solvent with a rotovap within the sample to produce a residue of solutes. g) A calibration curve is established using a standard solution with a dwell time set at 50 ms are completed. h) Quantifying an amount of one or more analytes in the sample using Liquid Chromatography with tandem mass spectrometry. Quantifying comprises quantifying the signal intensities detected for each analyte and comparing the signal intensities to a calibration curve for that analyte to determine the concentration of each analyte.

It is a further aspect of the present invention to provide a comprehensive, personalized analysis of breast milk composition, as well as individual dietary and supplement recommendations based on the results of the analysis.

Aspects of the present invention include a method of analyzing breast milk for a panel of analytes, comprising a) collecting a sample comprising breast milk from the human that produced the breast milk; b) analyzing the sample for a panel of nutritional analytes comprising one or more of: calcium, iron, Vitamin A, Vitamin C, Vitamin B 12, Vitamin D, Vitamin E, Vitamin K 1, Vitamin K2, Vitamin B1, Vitamin B2, vitamin B3, Vitamin B6, choline, folate, phosphorus, zinc, selenium, magnesium, cyanocobalamin, and environmental/toxic metals; aluminum, silicon, platinum, copper, cadmium, Lead, Mercury, Choline, Nickel, Beryllium, Boron and Hexavalent chromium. The panel of analytes can further comprise one or more fatty acids e.g., docosahexaenoic acid (DHA), arachidonic acid (ARA), Lactic Acid (LA), Eicosatetraenoic acid (EPA), and alpha-Linolenic acid (ALA), and c) providing the human with the results of the analyzed sample, wherein the results comprise a concentration of each analyte present in the sample. If the measured concentration of a nutrient analyte is in the panel of analytes is below guidance concentration for the nutrient analyte, then the human's breast milk has a deficiency of the analyte and if the measured concentration of a nutrient analyte in the panel of analytes is above a guidance concentration for the nutrient analyte, then the human's breast milk has an elevated level of the nutrient analyte. Guidance concentrations for nutrient analytes can comprise a concentration range.

Aspects of the present invention include methods of screening breast milk for a panel of nutrient analytes associated with diet, comprising: a) collecting a sample comprising breast milk from the human that produced the breast milk; b) analyzing the sample for concentration of one or more nutrient analytes; c) analyzing the sample for a concentration of one or more contaminant analytes; d) providing a dietary recommendation to the human based whether the measured concentration is above or below the guidance concentration for each nutrient analyte and each contaminant analyte. In an embodiment of the invention, nutrient analytes comprise one or more of: calcium, iron, Vitamin A, Vitamin C, Vitamin B 12, Vitamin D, Vitamin E, Vitamin K 1, Vitamin K2, Vitamin B 1, Vitamin B2, vitamin B3, Vitamin B6, thiamine, choline, folate, phosphorus, zinc, selenium, magnesium, cyanocobalamin. The nutrient analytes can further comprise a panel of analytes comprising one or more fatty acids e.g., docosahexaenoic acid (DHA), arachidonic acid (ARA), Lactic Acid (LA), Eicosatetraenoic acid (EPA), and alpha-Linolenic acid (ALA). Guidance concentration ranges have been discovered and Table 1 provides guidance concentrations for nutrient analytes.

TABLE 1

Guidance Concentrations of Nutrient Analytes.

| Nutrient Analyte | Guidance concentration lower range | Guidance concentration upper range |
|---|---|---|
| Calcium bound to protein | 5 mg/dL | 45 mg/dL |
| Ionized calcium | 155 mg/dl | 300 mg/dL |
| Iron | 0.01 mg/L | 1 mg/L |
| Vitamin A | 229 µg/L | 1090 µg/L |
| Vitamin C | 10 mg/L | 158 mg/L |
| Vitamin D | 0.90 nM/L | 1.42 nM/L |
| Vitamin B 12 | 0.1 µg/L | 2 µg/L |
| Vitamin E | 5 umol/L | 100 umol/L |
| Vitamin K1 | 0.5 umol/L | 100 umol/L |
| Vitamin K2 | 0.5 umol/L | 100 umol/L |
| Vitamin B1 (thiamine) | 0.05 mg/L | 200 mg/L |
| Vitamin B2 (riboflavin) | 10 ug/L | 1000 ug/L |
| Vitamin B3 (niacin) | 50 ug/L | 1000 ug/L |
| Vitamin B6 | 0.01 mg/L | 100 mg/L |
| Choline | 50 umol/L | 1000 umol/L |
| Vitamin B9 (Folate) | 8-120 ug/L | 8-120 ug/L |
| Phosphorus | 0.0001 mg/L | 10 mg/L |
| Zinc | 0.001 mg/L | 50 mg/L |
| Magnesium | 0.001 mg/L | 50 mg/L |
| Cyanocobalamin | 0.0001 mg/L | 10 mg/L |
| DHA | 0.01 to 0.5% of total fatty acids, | |
| Analyte is linoleic acid (LA) | 3000 nmol/ml | 8000 nmol/ml |
| Arachidonic acid (ARA) | 3000 nmol/ml | 8000 nmol/ml |
| Alpha-linoleic acid (ALA) | 350 nmol/L | 800 nmol/ml |

Guidance concentrations of contaminant analytes have been established for environmental toxins and toxic metals, such as but not limited to aluminum, silicon, platinum, copper, cadmium, Lead, Mercury, arsenic, Nickel, Beryllium, Boron and Hexavalent chromium

TABLE 2

Guidance Concentrations of Contaminant Analytes.

| Contaminant Analyte | Guidance concentration lower range | Guidance concentration upper range | Lower Detection Limit of ICP-MS |
|---|---|---|---|
| Aluminum | 0.0001 mg/L | 0.05 mg/L | 1 ppT |
| Silicon | 0.0001 mg/L | 4 mg/L | 1 ppT |
| Platinum | 0.0001 mg/L | 0.003 mg/L | 1 ppT |
| Copper | 0.0001 mg/L | 0.05 mg/L | 1 ppT |
| Cadmium | is 0.005 mg/L | to 0.2 mg/L | 1 ppT |
| Lead | 0.0001 mg/L | 0.015 mg/L | 1 ppT |
| Mercury | 0.0001 mg/L | 0.002 mg/L | 1 ppT |
| Arsenic | is 0.0001 to 0.01 mg/L | 0.01 mg/L | 1 ppT |
| Nickel | 0.0001 to 0.05 mg/L | 0.05 mg/L | 1 ppT |
| Beryllium | from 0.0001 to 0.05 mg/L | 0.05 mg/L | 1 ppT |
| Boron | 0.0001 to 0.05 mg/L | 0.05 mg/L | 1 ppT |
| Chromium | 0.0001 to 0.05 mg/L | 0.05 g/L | 1 ppT |

It has been discovered through analysis, that the nutritional content of breast milk varies widely between people and over time in the same person. We have found that collecting samples through a 24-hour period from the same individual throughout various manual or machine expression methods provides a representative sample. Further, maternal diet affects the analytes including but not limited to analytes listed in Table 1 and Table 2.

Lactating mothers can receive their analytical results with personalized dietary recommendations to increase the concentration of vitamins and minerals and decrease the concentration of toxins in their breast milk.

In some embodiments, the method further comprises re-testing the human's breast milk by repeating steps of the method every 1-8 weeks for the duration of lactation. Re-testing the human's breast milk periodically can improve the overall health and diet of the human. Re-testing the human's breast milk periodically and providing dietary recommendations is configured to increase the human's chances of prolonging breastfeeding. Re-testing the human's breast milk periodically and providing dietary/lifestyle recommendations is configured to improve the quality of the human's breast milk. Providing dietary recommendations is configured to decrease the level of anxiety and/or stress and provide feedback to the human associated with breastfeeding. Testing under the method of the invention can be repeated to provide insight as to the effect of dietary changes and make further dietary recommendations. The process of testing and providing feedback can continue through the lactation period of the nursing individual.

Reference ranges for each micronutrient are shown in Table 1 and the breastfeeding mother can be informed of her results as compared to the average. Lifestyle and dietary recommendations can be reviewed by a team of physicians to provide recommendations on how to improve the concentrations of nutrient analytes in human milk. It has been discovered that maternal diet impacts nutrient concentrations in breast milk, and a mother has the ability to change her diet to affect the concentration of said nutrient concentrations. It has been discovered that nutrient concentrations in breast milk is variable and information about the composition of an individual's milk is useful for making dietary decisions and nursing decisions.

The operations described herein can be performed in any sensible order. Any operations not required for proper operation can be optional. Further, all methods described herein can also be stored on a computer readable storage to control a computer. The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method for analyzing breast milk for total fatty acid concentrations comprising the steps of:
   a) collecting a human breast milk sample from a lactating individual;
   b) freezing the breast milk sample at a temperature between −70 degrees C. to −80 degrees C.;
   c) thawing the breast milk sample above 20 degrees C.;
   d) homogenizing the breast milk sample by sonicating to disrupt cell structures in the breast milk sample;
   e) performing liquid liquid extraction by combining the breast milk sample with chloroform, methanol, and water in a volume ratio of approximately 1:2:0.8 in a separating vessel to form an upper layer and a lower layer;
   f) separating the lower layer containing chloroform and lipids;
   g) dissolving the lower layer in a nonpolar solvent;
   h) adding boron trichloride in methanol to form an extract mixture;
   i) heating the extract mixture at about 60 degrees C. for approximately ten minutes;
   j) cooling the extract mixture with water and hexane and mixing;
   k) extracting an upper organic layer to provide a sample extract; and
   l) performing gas chromatography-mass spectrometry analysis on the sample extract to provide measured total fatty acid concentrations.

2. The method of claim 1 wherein the step of collecting a human breast milk sample comprises collection of breast milk over a 24 hour period.

3. The method of claim 1 wherein the nonpolar solvent of step g) comprises hexane.

4. The method of claim 3 wherein the concentration of boron trichloride in methanol is 12% weight/weight.

* * * * *